United States Patent [19]

Ciaglia et al.

[11] Patent Number: 5,258,003
[45] Date of Patent: Nov. 2, 1993

[54] METHOD AND APPARATUS FOR INDUCTION OF PNEUMOPERITONEUM

[75] Inventors: Pasqule Ciaglia, Utica; John S. Gentelia, Madison, both of N.Y.

[73] Assignee: Conmed Corporation, Utica, N.Y.

[21] Appl. No.: 891,033

[22] Filed: Jun. 1, 1992

[51] Int. Cl.$^5$ ............................................. A61M 5/18
[52] U.S. Cl. ................................. 606/185; 604/164; 604/264
[58] Field of Search ................ 606/108, 184, 185; 604/117, 157, 164, 165, 169, 158, 264, 272, 273, 274

[56] References Cited

U.S. PATENT DOCUMENTS

| | | | |
|---|---|---|---|
| 4,191,191 | 3/1980 | Auburn | 606/185 |
| 4,931,042 | 6/1990 | Holmes et al. | 606/185 |
| 5,009,643 | 4/1991 | Reich et al. | 604/165 |
| 5,104,382 | 4/1992 | Brinkerhoff et al. | 604/165 |
| 5,139,486 | 8/1992 | Moss | 604/164 |
| 5,147,376 | 9/1992 | Pianetti | 606/185 |

*Primary Examiner*—Stephen C. Pellegrino
*Assistant Examiner*—William Lewis
*Attorney, Agent, or Firm*—Larson & Taylor

[57] ABSTRACT

A method and apparatus for induction of pneumoperitoneum and insertion of a laparoscopic sheath is provided in which a trocar carrying a sheath or cannula has a tapered distal end with screw threads formed on the outer surface of the distal end. The distal tip or end terminates in a short flexible tube. A hollow needle extends through a central passageway in the trocar and through the flexible tip on the trocar. The opposite end of the hollow needle is provided with a pressure chamber which is in fluid communication with the passageway in the needle. In use, the trocar and cannula are screwed into the body tissues of the patient and when the distal end of the needle enters the peritoneal space within the body, liquid within the pressure chamber passes through the hollow needle and into the peritoneal space. The release of the fluid from the pressure chamber is an indicator to the surgeon that the end portion of the needle has entered the peritoneal space. The trocar and cannula are then screwed in as the needle is withdrawn from the flexible tip on the distal end of the trocar so as to prevent damage to any body tissues. Induction of an adequate pneumoperitoneum may then take place after verifying proper placement of the trocar and cannula. Instruments suitable for laparoscopic surgery may be inserted through the cannula or sheath.

7 Claims, 1 Drawing Sheet

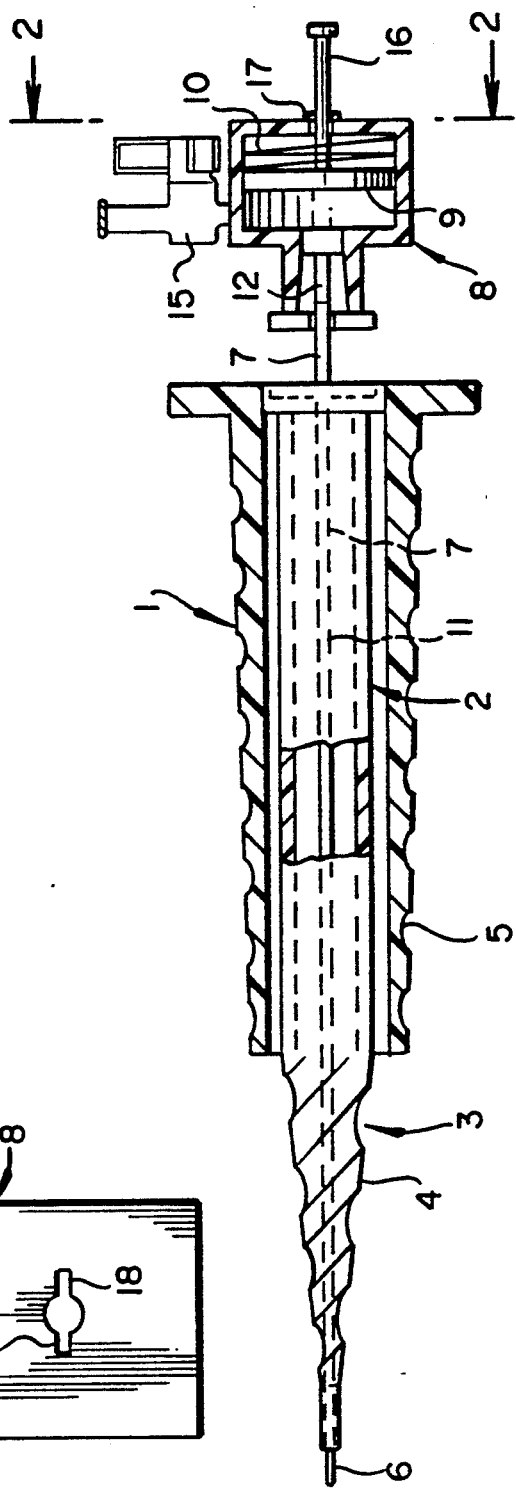
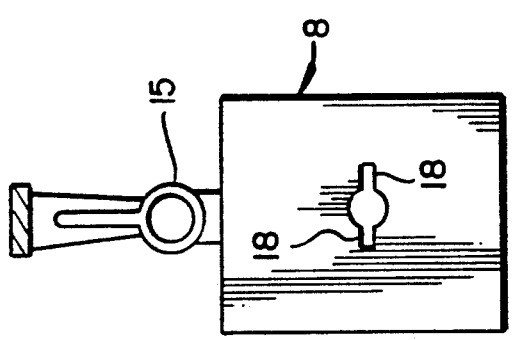

METHOD AND APPARATUS FOR INDUCTION OF PNEUMOPERITONEUM

BACKGROUND OF THE INVENTION

In the past, percutaneous tube placements have been utilized to evacuate fluid collections or to form a passageway to insert a laparoscopic sheath. In all of these procedures, even though the trocar has three sharp edges, more than a moderate force is often needed to insert the trocar cannula. This poses a clear danger in that, with the sudden lack of resistance after penetration through resistant tissue, the instrument may be driven in too far and may cause serious damage to a viscus. In the case of the pleural cavity, one may injure the lung, heart or spleen and in the abdomen there is danger of injuring the intestine, aorta or other body structure. The trocar and cannula require the axial force necessary to cut through and dilate the tissues. In order to obtain the desired dilation and outward spread, the use of the conventional trocar and cannula results in a dangerous axial force or thrust.

Typical cannula and trocar assemblies are shown in such patents as Deniega U.S. Pat. No. 5,066,288, Holmes et al U.S. Pat. No. 4,931,042 and Knepshield et al U.S. Pat. No. 4,177,814. The Albertini U.S. Pat. No. 4,670,008 discloses a needle for injecting or removing liquid from a body comprising a trocar having a sharpened end disposed within a cannula with the external surface of the cannula having threads on its end to facilitate insertion. However, these devices do not provide an adequate solution to the problem of enabling the surgeon to determine precisely when the trocar has reached the desired body cavity so as to prevent damage to other body tissues.

SUMMARY OF THE INVENTION

According to the present invention, there is provided a trocar having screw threads on the distal end of the trocar with a short section of a flexible tube on the distal end. A hollow needle extends through a passageway in the trocar with the needle point extending through the flexible tube on the distal end of the trocar.

At the proximal end of the trocar there is provided a chamber in fluid communication with the passageway within the needle. The chamber is provided with a spring pressed piston which is urged to force any fluid within the chamber into the passageway in the needle. A plunger is mounted on the piston so that the piston may be rotated from a locked inoperative position to an unlocked operative position to force fluid within the chamber through the passageway in the needle.

In use, the plunger and piston are rotated to a locked position and the pressure chamber is filled with a liquid. The surgeon places the distal end of the trocar against the skin and rotates the plunger to release the spring pressed piston so as to force the pressurized fluid into the passageway in the needle. The fluid does not pass through the distal end of the trocar as it is blocked by the skin of the patient. The surgeon then rotates the trocar through a small skin incision so that the screw threads on the distal end of the trocar engage the tissues. The surgeon continues to rotate the trocar and cannula until the distal end of the needle protruding from the end of the trocar reaches the peritoneum. When the peritoneum is reached, the liquid within the pressure chamber is forced through the distal end of the needle into the peritoneum. The discharge of the fluid from the pressure chamber is an indicator to the surgeon that the distal end of the trocar has reached the abdominal cavity. The surgeon then continues to rotate the trocar and so that the screw threads move the trocar and cannula further into the peritoneum while the surgeon, at the same time, withdraws the needle slightly so as to prevent further movement of the needle into the peritoneum. Thus, the point of the needle is drawn back from the flexible tube at the distal end of the trocar, thus leaving only the flexible tube in place. This flexible tip on the end of the trocar prevents damage to any adjacent tissues within the peritoneum. In this position, induction of an adequate pneumoperitoneum may take place through the needle after verifying a proper placement.

An object of the present invention is to provide a trocar and needle combination which will quickly provide an opening in the peritoneum for induction of pneumoperitoneum and insertion of a cannula for laparoscopic surgery without endangering body tissues.

Another object of the present invention is to provide a mechanism for a trocar which will provide a signal to the surgeon when the distal end of the trocar has reached the peritoneum.

Other objects and many of the attendant advantages of the present invention will become more readily apparent upon consideration of the following detailed specification together with the accompanying drawings wherein:

BRIEF DESCRIPTION OF THE DRAWING

FIG. 1 is a longitudinal sectional view of a screw trocar and cannula according to the present invention; and FIG. 2 is a plan view of the pressurized chamber and locking mechanism used with the screw trocar.

DETAILED DESCRIPTION OF THE PREFERRED EMBODIMENT

Referring now more specifically to the drawing, there is shown a cannula 1 having a trocar 2 which slidably fits within the cannula.

The trocar 2 has a tapered end portion 3 with screw threads 4 formed on the outer surface of the tapered end portion. The distal tip end of the trocar 2 has affixed thereto a flexible tube 6.

A hollow needle 7 is slidably disposed within the trocar 2 and extends through the distal end of the trocar and through the soft plastic tube 6. The opposite end of the needle 7 extends beyond the proximal end portion of the trocar 2 and has attached thereto a pressure chamber 8. The pressure chamber 8 is provided with a piston 9 and spring 10 with a passageway interconnecting the pressure chamber 8 with the passageway 11 extending throughout the length of the needle 7. There is provided a stopcock and port 15 mounted on the chamber 8 for introducing saline solutions or other fluids into the chamber 8. There is provided a plunger 16 which is rotatably attached to the piston 9 and extend upwardly through the opening in the top wall of chamber 8. The plunger 16 is provided with a pair of wings 17 affixed thereto which are adapted to slide through slots 18 in the top wall of the chamber 8, FIG. 2. Thus, when the plunger 16 is drawn upwardly to compress spring 10 and the plunger rotated so that the wings 17 are not in alignment with the slots 18 the piston is retained in an inoperative position.

In use, the pressure chamber 8 is filled with fluid through the port 15 with the piston retained in an inoperative position. The needle 7 is inserted into the trocar 1 and extends through the flexible tube 6 on the end portion of the trocar. When the surgeon is ready to commence cutting through the body tissues, the surgeon holds the distal end of the trocar against the skin and rotates the plunger 16 so that the spring pressed piston 9 forces the fluid in the chamber 8 into the passageway 11 within needle 7. The surgeon then rotates the trocar and cannula while applying pressure to form a opening passageway in the tissues. As the trocar is rotated, the screw threads 4 draw the trocar further into the body tissue until the needle 7 within the trocar 1 pierces the peritoneum. When the needle 7 reaches this position, the pressurized fluid within the pressure chamber 8 forces the fluid through the needle passageway 11 and into the peritoneum. The descent of the fluid within the pressure chamber indicates to the surgeon that the peritoneum has been reached and the surgeon then rotates the trocar 1 while withdrawing the needle 7 slightly so as to remove the needle 7 from the flexible tip 6. With the needle 7 removed from the flexible tip 6, no damage to adjacent tissue is possible even with further movements of the trocar. The needle may then be withdrawn and pressurized gas may be passed through the channel in the trocar and into the peritoneal cavity to obtain an adequate pneumoperitoneum. The cannula 1 may then be rotated and secured within the body opening provided by the trocar. The trocar may then be removed and the cannula 1 may then be used for insertion of laparoscopic instruments.

Obviously many modifications and variations of the present invention are possible in light of the above teachings.

What is claimed as new and is desired to be secured by Letters Patent is:

1. A device for induction of pneumoperitoneum and introduction of a laparoscopic sheath comprising, in combination, a cannula, a trocar, a tapered distal end on said trocar, a flexible tube disposed on the tip of the distal end of the trocar, a needle extending through a passageway in the trocar, one end of the needle extending through the flexible tube on the distal end of the trocar, a pressure chamber and spring pressed piston mounted on the other end of the needle whereby when the distal end of the trocar enters the peritoneal space the pressure chamber provides an indicator of the entry by movement of the piston downwardly.

2. A device according to claim 1 and further including screw threads on the external surface of the tapered distal end of the trocar.

3. A device according to claim 1 and further including a stopcock on said chamber to introduce fluids into the peritoneal space.

4. A method for induction of pneumoperitoneum and insertion of a laparoscopic cannula in a patient wherein a cannula is disposed over a trocar having a tapered distal end with screw threads on the external surface of the distal end, a short flexible tube on the tip of the distal end of the trocar, a hollow needle extending through a passageway in the trocar and a pressure chamber mounted on a proximal end of the needle, comprising the steps of locating the needle with a distal end extending through the tip of the flexible tube, rotating the trocar to cause the screw threads on the distal end of the trocar to puncture tissue of the patient, discontinuing the rotation of the trocar when the pressure chamber signals that the distal end of the needle has passed into the peritoneum of the patient, rotating the trocar while withdrawing the needle so that the flexible tip on the distal end of the trocar may enter the peritoneum and assume a curved position to prevent damage to body tissue and subsequently inducing pneumoperitoneum by passing pressurized gas through the needle into the peritoneal cavity of the patient.

5. A method according to claim 4 and further including the step of removing the trocar from the cannula while sliding the cannula into the peritoneal cavity.

6. A method according to claim 4 wherein the cannula has screw threads on the external surface so that the cannula may be rotated into the body opening provided by the trocar.

7. A method according to claim 6 wherein when the trocar is removed and the cannula is within the body opening provided by the trocar laparoscopic instruments may be inserted through the cannula.

* * * * *